United States Patent
Reicher et al.

(10) Patent No.: US 11,244,746 B2
(45) Date of Patent: Feb. 8, 2022

(54) AUTOMATICALLY ASSOCIATING USER INPUT WITH SECTIONS OF AN ELECTRONIC REPORT USING MACHINE LEARNING

(71) Applicant: International Business Machines Corporation, Armonk, NY (US)

(72) Inventors: Murray A. Reicher, Rancho Santa Fe, CA (US); Marwan M. Sati, Mississauga (CA); Mark D. Bronkalla, Waukesha, WI (US); Michael Trambert, Santa Barbara, CA (US)

(73) Assignee: INTERNATIONAL BUSINESS MACHINES CORPORATION, Armonk, NY (US)

( * ) Notice: Subject to any disclaimer, the term of this patent is extended or adjusted under 35 U.S.C. 154(b) by 546 days.

(21) Appl. No.: 15/669,177

(22) Filed: Aug. 4, 2017

(65) Prior Publication Data

US 2019/0042703 A1 Feb. 7, 2019

(51) Int. Cl.
*G06F 17/00* (2019.01)
*G16H 15/00* (2018.01)
*G06N 20/00* (2019.01)
*G16H 10/60* (2018.01)
*G16H 30/20* (2018.01)

(52) U.S. Cl.
CPC ............ *G16H 15/00* (2018.01); *G06N 20/00* (2019.01); *G16H 10/60* (2018.01); *G16H 30/20* (2018.01)

(58) Field of Classification Search
CPC ...... G06F 19/321; G16H 15/00; G16H 10/60; G16H 30/20; G06N 20/00
See application file for complete search history.

(56) References Cited

U.S. PATENT DOCUMENTS 6,574,629 B1 * 6/2003 Cooke, Jr. ............... G06F 16/40
8,195,594 B1 * 6/2012 Bryce .................... G16H 15/00
706/47

(Continued)

FOREIGN PATENT DOCUMENTS

EP 2169577 A1 3/2010

OTHER PUBLICATIONS

Zimmerman, S. L., Kim, W., & Boonn, W. W. (2011), Informatics in radiology: automated structured reporting of imaging findings using the AIM standard and XML, RadioGraphics, 31(3), 881-887.

(Continued)

*Primary Examiner* — Mohammed H Zuberi
(74) *Attorney, Agent, or Firm* — Michael Best & Friedrich LLP

(57) ABSTRACT

Systems and methods for generating electronic reports for medical images. One system includes an electronic processor configured to access a plurality of prior reports associated with a user and automatically generate a mapping using machine learning based on the plurality of prior reports. The mapping associates language included in the plurality of prior reports with at least one section of a report. The system stores the mapping to a memory, receives input from the user for an electronic report associated with a medical image, accesses the mapping from the memory, automatically determines a section in the electronic report associated with the input based on the mapping, and automatically inserts text into the section in the electronic report based on the input.

19 Claims, 5 Drawing Sheets

(56) References Cited

U.S. PATENT DOCUMENTS

| | | | |
|---|---|---|---|
| 8,320,651 B2 | 11/2012 | Vining et al. | |
| 8,498,870 B2 | 7/2013 | Brandt | |
| 8,645,157 B2* | 2/2014 | Giles | G06Q 50/22 |
| | | | 705/2 |
| 8,706,680 B1* | 4/2014 | Macfarlane | G06F 17/2229 |
| | | | 707/603 |
| 9,014,485 B2 | 4/2015 | Moehrle | |
| 9,786,051 B2* | 10/2017 | Harper | G06F 16/51 |
| 2002/0082868 A1* | 6/2002 | Pories | G06F 19/324 |
| | | | 705/3 |
| 2003/0179223 A1* | 9/2003 | Ying | G06F 3/0482 |
| | | | 715/702 |
| 2007/0005643 A1* | 1/2007 | Korman | G06F 19/3456 |
| 2007/0043597 A1* | 2/2007 | Donaldson | G06F 19/3418 |
| | | | 705/3 |
| 2007/0053567 A1* | 3/2007 | Adachi | G06F 19/321 |
| | | | 382/128 |
| 2008/0046286 A1* | 2/2008 | Halsted | G06Q 50/22 |
| | | | 705/2 |
| 2008/0114618 A1* | 5/2008 | Pysnik | G06Q 10/10 |
| | | | 705/3 |
| 2008/0114689 A1* | 5/2008 | Psynik | G16H 15/00 |
| | | | 705/51 |
| 2008/0201372 A1* | 8/2008 | Fukatsu | G06F 19/321 |
| 2008/0221923 A1* | 9/2008 | Shogan | G06Q 50/22 |
| | | | 705/2 |
| 2009/0164474 A1* | 6/2009 | Noumeir | G06F 19/321 |
| 2009/0187407 A1* | 7/2009 | Soble | G10L 15/26 |
| | | | 704/260 |
| 2009/0287487 A1* | 11/2009 | Rossman | G16H 30/40 |
| | | | 704/235 |
| 2011/0002515 A1* | 1/2011 | Futami | G06F 19/321 |
| | | | 382/128 |
| 2012/0035963 A1 | 2/2012 | Qian et al. | |
| 2013/0151286 A1* | 6/2013 | Kablotsky | G06F 19/321 |
| | | | 705/3 |
| 2013/0311200 A1* | 11/2013 | Cohen-Solal | G06F 19/321 |
| | | | 705/2 |
| 2013/0311472 A1* | 11/2013 | Cohen-Solal | G06F 19/321 |
| | | | 707/737 |
| 2014/0142939 A1* | 5/2014 | Aradi | G10L 15/26 |
| | | | 704/235 |
| 2014/0149407 A1* | 5/2014 | Qian | G06F 19/321 |
| | | | 707/737 |
| 2014/0172456 A1* | 6/2014 | Qian | G06F 16/24 |
| | | | 705/3 |
| 2014/0316822 A1* | 10/2014 | Kleeman | G06F 16/2228 |
| | | | 705/3 |
| 2014/0379374 A1* | 12/2014 | Vinals | G16H 10/60 |
| | | | 705/3 |
| 2015/0142462 A1* | 5/2015 | Vaidya | G06F 19/3418 |
| | | | 705/2 |
| 2015/0161329 A1* | 6/2015 | Mabotuwana | G06F 19/321 |
| | | | 705/3 |
| 2015/0310455 A1* | 10/2015 | Vinals | G06Q 50/22 |
| | | | 705/2 |
| 2015/0347705 A1* | 12/2015 | Simon | G16H 10/60 |
| | | | 705/3 |
| 2016/0012319 A1* | 1/2016 | Mabotuwana | G06K 9/72 |
| | | | 382/128 |
| 2016/0092656 A1 | 3/2016 | Glaser-Seidnitzer et al. | |
| 2016/0147971 A1* | 5/2016 | Kolowitz | G06F 3/0481 |
| | | | 715/753 |
| 2016/0283657 A1* | 9/2016 | Bhotika | G16H 15/00 |
| 2017/0061100 A1* | 3/2017 | Sati | G06F 19/321 |
| 2017/0177795 A1* | 6/2017 | Mabotuwana | G06F 19/321 |
| 2018/0039760 A1* | 2/2018 | Armbruster | G06F 17/248 |
| 2018/0137177 A1* | 5/2018 | Belcher | G16H 10/60 |
| 2018/0182476 A1* | 6/2018 | Babu | G16H 15/00 |
| 2019/0042703 A1* | 2/2019 | Reicher | G06N 20/00 |
| 2019/0108905 A1* | 4/2019 | Zhang | G06F 19/321 |
| 2019/0139642 A1* | 5/2019 | Roberge | G06K 9/3233 |

OTHER PUBLICATIONS

Wilkowski, B., Pereira, Ó. N. M., Dias, P. M. et al. (2008), Miaware Software: 3D Medical Image Analysis with Automated Reporting Engine and Ontology-based Search.

* cited by examiner

FINDINGS:
LUNGS: Normal. No visible pulmonary disease.
VASCULATURE: Normal. Thrombus cannot be excluded without intravenous contrast.
HILA: Normal. No mass or adenopathy.
MEDIASTINUM: Normal. No mass or adenopathy.
CARDIAC: Normal. No enlargement, pericardial thickening, or significant calcification.
PLEURA: Normal. No mass or effusion.
CHEST WALL: Normal. No mass or axillary adenopathy.
LIVER: Normal. No enlargement, atrophy, abnormal density, or significant focal lesion.
BILIARY: Normal. No dilatation or calcification.
PANCREAS: Normal. No lesion, fluid collection, ductal dilatation, or atrophy.
SPLEEN: Normal. No enlargement or focal lesion.
KIDNEYS: Normal. No mass, obstruction, or calcification.
ADRENALS: Normal. No mass or enlargement.
AORTA/VASCULAR: Normal. No aneurysm.
RETROPERITONEUM: Normal. No mass or adenopathy.
BOWEL/MESENTERY: Normal. No visible mass, obstruction, or bowel wall thickening.
ABDOMINAL WALL: Normal. No mass or hernia.
BONES: Normal. No bony lesion or fracture.
OTHER: Negative.

AUTOMATICALLY ASSOCIATING USER INPUT WITH SECTIONS OF AN ELECTRONIC REPORT USING MACHINE LEARNING

FIELD

Embodiments described herein relate to systems and methods for generating electronic reports, such as for medical images. More specifically, embodiments herein relate to automatically associating user input with sections of an electronic report using machine learning.

SUMMARY

When a reviewer interprets a medical imaging exam to create an electronic report, the reviewer's attention is divided between the images and the report. For example, the report is often displayed within a separate window or on a separate display device than the images. Thus, each time the reviewer has data (a finding) to enter into the report, the reviewer must switch his or her attention from the displayed images to the report. This division of tasks results in eye and head movements as the reviewer switches attention between the images and report, which accentuates fatigue, associated cognitive biases, and perceptual errors.

To solve these and other problems, embodiments described herein provide methods and systems for automatically associating user input with sections of an electronic report using machine learning. The system and methods generate mappings using machine learning. The mappings associate findings (user input received via a mouse, keyboard, a microphone, or another input mechanism) with one or more sections of an electronic report such that the reviewer does not need to select a section in the report in which to place report findings.

For example, one embodiment provides a system for generating an electronic report of a medical image or imaging exam. The system includes an electronic processor configured to access a plurality of prior reports associated with a user and automatically generate a mapping using machine learning based on the plurality of prior reports. The mapping associates language included in the plurality of prior reports with at least one section of a report. The system stores the mapping to a memory, receives input from the user for an electronic report associated with a medical image, accesses the mapping from the memory, automatically determines a section in the electronic report associated with the input based on the mapping, and automatically inserts text into the section in the electronic report based on the input.

Another embodiment provides a method for generating an electronic report for a medical image generated as part of a medical imaging exam. The method includes accessing, with an electronic processor, a plurality of prior reports associated with a user and automatically, with the electronic processor, generating a mapping using machine learning based on the plurality of prior reports. The mapping associates language included in the plurality of prior reports with at least one section of a report. The method also includes storing the mapping to a memory, receiving input from the user for an electronic report associated with a medical image, accessing the mapping from the memory, automatically determining a section in the electronic report associated with the input based on the mapping, and automatically generating and displaying a window. The window includes text to be inserted into the section of the electronic report, an identifier of the section of the electronic report, and a selection mechanism for validating the text to be inserted into the section of the electronic report. The method further includes automatically inserting the text into the section in the electronic report based on the input in response to selection of the selection mechanism.

Another embodiment provides a non-transitory, computer-readable medium storing instructions that, when executed by an electronic processor, perform a set of functions. The set of functions includes accessing a plurality of prior reports associated with a user and automatically generating a mapping using machine learning based on the plurality of prior reports. The mapping associates language included in the plurality of prior reports with at least one section of a report. The set of functions further includes storing the mapping to a memory, receiving input from the user for an electronic report associated with a medical image, accessing the mapping from the memory, automatically determining a section in the electronic report associated with the input based on the mapping, and automatically inserting text into the section in the electronic report based on the input. The set of functions also includes receiving feedback associated with the text and automatically updating the mapping based on feedback.

Other aspects of the invention will become apparent by consideration of the detailed description and accompanying drawings.

BRIEF DESCRIPTION OF THE DRAWINGS

FIG. 4 illustrates an example electronic report generated by the system of FIG. 2 using the method of FIG. 3.

DETAILED DESCRIPTION

One or more embodiments are described and illustrated in the following description and accompanying drawings. These embodiments are not limited to the specific details provided herein and may be modified in various ways. Furthermore, other embodiments may exist that are not described herein. Also, the functionality described herein as being performed by one component may be performed by multiple components in a distributed manner. Likewise, functionality performed by multiple components may be consolidated and performed by a single component. Similarly, a component described as performing particular functionality may also perform additional functionality not described herein. For example, a device or structure that is "configured" in a certain way is configured in at least that way, but may also be configured in ways that are not listed. Furthermore, some embodiments described herein may include one or more electronic processors configured to perform the described functionality by executing instructions stored in non-transitory, computer-readable medium. Similarly, embodiments described herein may be implemented as non-transitory, computer-readable medium storing instructions executable by one or more electronic processors to perform the described functionality. As used in the present application, "non-transitory computer-readable medium" comprises all computer-readable media but does not consist of a transitory, propagating signal. Accordingly, non-transitory computer-readable medium may include, for example, a hard disk, a CD-ROM, an optical storage device, a magnetic storage device, a ROM (Read Only Memory), a RAM (Random Access Memory), register memory, a processor cache, or any combination thereof.

In addition, the phraseology and terminology used herein is for the purpose of description and should not be regarded as limiting. For example, the use of "including," "containing," "comprising," "having," and variations thereof herein is meant to encompass the items listed thereafter and equivalents thereof as well as additional items. The terms "connected" and "coupled" are used broadly and encompass both direct and indirect connecting and coupling. Further, "connected" and "coupled" are not restricted to physical or mechanical connections or couplings and can include electrical connections or couplings, whether direct or indirect. In addition, electronic communications and notifications may be performed using wired connections, wireless connections, or a combination thereof and may be transmitted directly or through one or more intermediary devices over various types of networks, communication channels, and connections. Moreover, relational terms such as first and second, top and bottom, and the like may be used herein solely to distinguish one entity or action from another entity or action without necessarily requiring or implying any actual such relationship or order between such entities or actions.

Figure 1A:
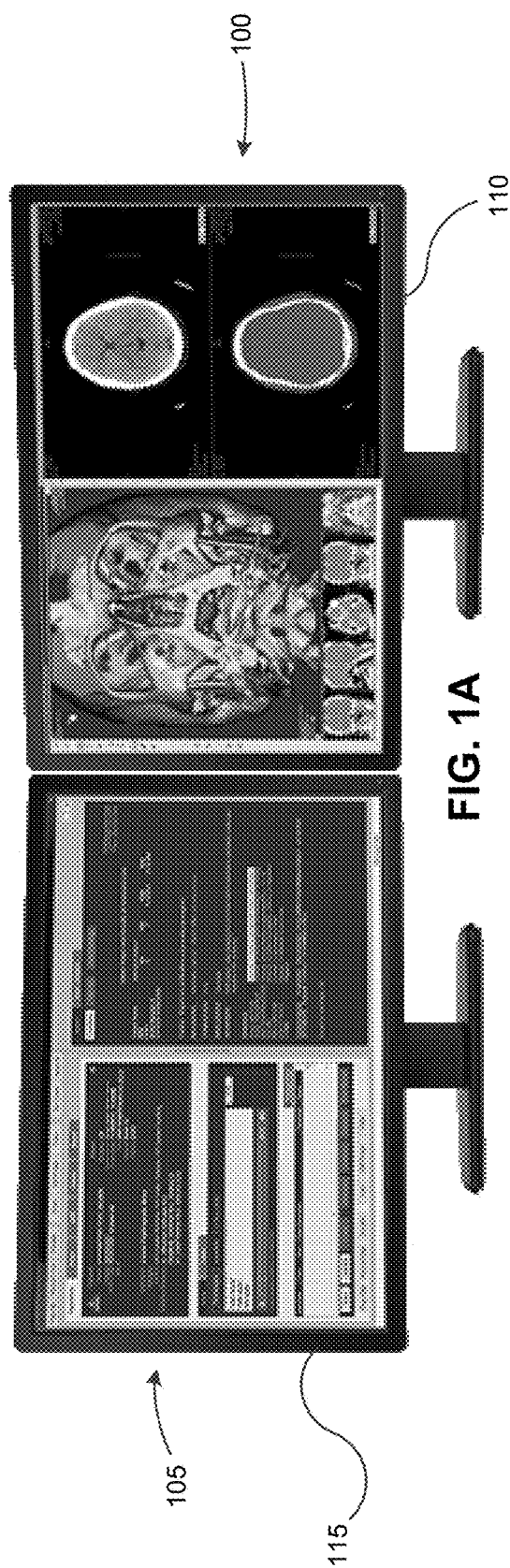
FIG. 1A illustrates a set of display devices displaying images and a report template.

As described above, a reviewer analyzing medical images may need to quickly and frequently change his or her focus and attention between the medical images and an electronic report. Such a division in focus causes fatigue and other perceptual problems related to saccadic eye movements and division of attention, which can lead to errors in the report. For example, FIG. 1A illustrates a first display device 100 and a second display device 105. The first display device 100 displays a set of medical images 110, and the second display device 105 displays an electronic report 115 associated with the medical images 110. Thus, each time a reviewer analyzing the medical images 110 needs to record a finding within the electronic report 115, he or she must break concentration and gaze from the first display device 100 and view and focus on the second display device 105.

Figure 1B:
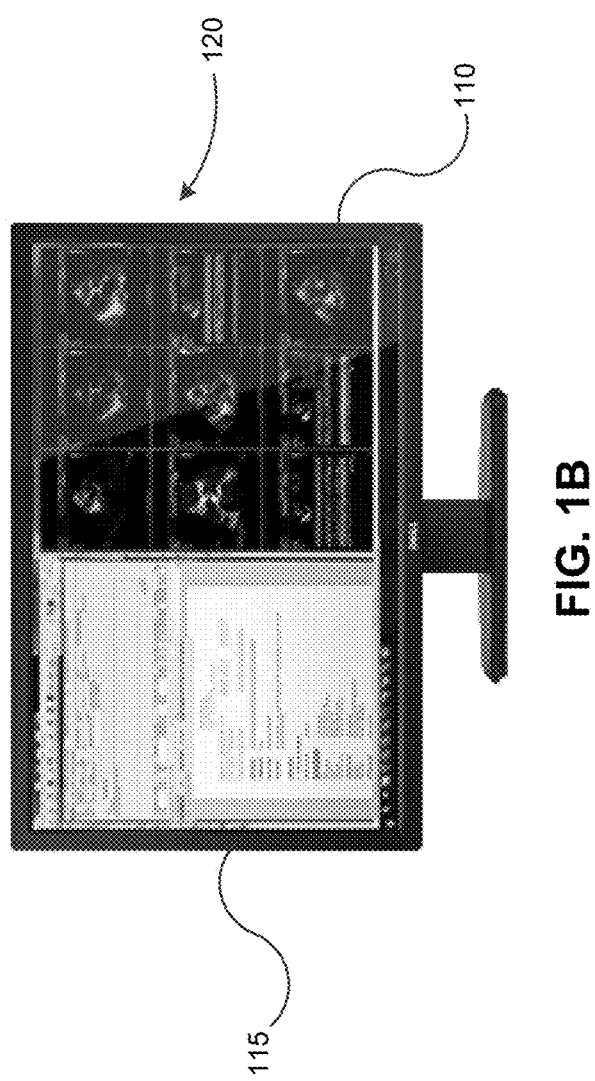
FIG. 1B illustrates a single display device displaying images and a report template.

Displaying both the images 110 and the report 115 on one display device does not solve this problem. For example, FIG. 1B illustrates a single display device 120. The right side of the display device 120 displays the images 110, and the left side of the display device 120 displays the electronic report 115. Accordingly, even in this configuration, a reviewer must change his or her focus and gaze on different portions of the display device 120. Also, displaying the images 110 and the report 115 on a single display device 120 may make the size of the images 110 and text within the report 115 so small that the reviewer experiences additional fatigue and visual strain.

In some embodiments, the electronic report is unstructured, where a reviewer inputs findings (via a mouse, keyboard, speaker, or other input mechanism). In other embodiments, the electronic report is structured and may be represented as an itemized or structured template. Although such report templates allow reviewers to generate more standardized reports and prevent some errors, the templates may increase the reviewer fatigue. For example, in addition to switching attention between images and the associated report, the reviewer must also select the appropriate section (line item) within the report template to insert a report finding. Similarly, although some reporting applications may be configured automatically or more accurately generate text for insertion in a report template (for example, based on contextual information), these applications still require a reviewer to divide his or her attention and focus between two separate windows or display devices to place findings within a report template.

To address these and other issues, embodiments described herein provide computerized methods and systems that automate the population of proper sections (line items or discrete elements) within a structured report. For example, the systems and methods described herein automatically generate mappings that associate particular user input (particular findings) to particular sections of an electronic report. Accordingly, based on the mappings, text is automatically inserted into an electronic report such that the user does not need to divide his or her attention between the images and the electronic report. Thus, as a user generates (dictates) a new report, the systems and methods apply the mappings to automatically parse input and insert input to the appropriate sections of an electronic report. As described in more detail below, the systems and methods access prior electronic reports and use machine learning to automatically generate mappings and update mapping as the systems and methods learn associations between particular user input and particular report sections.

Figure 2:
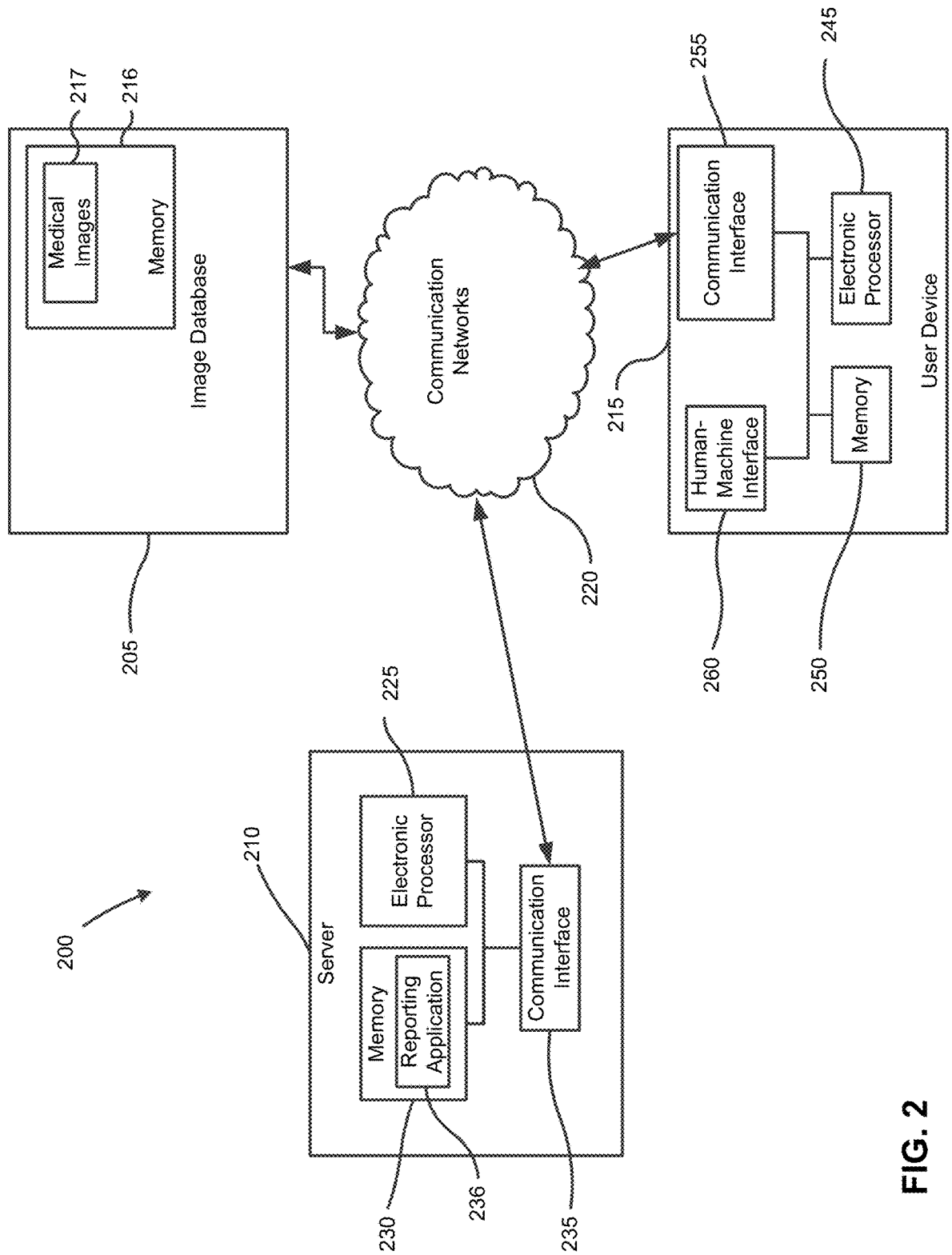
FIG. 2 schematically illustrates a system for generating electronic reports for medical images according to one embodiment.

For example, FIG. 2 schematically illustrates a system 200 for generating electronic reports for medical images according to one embodiment. The system 200 includes an image database 205, a server 210, and a user device 215. As illustrated in FIG. 2, the image database 205, the server 210, and the user device 215 are communicatively coupled through a communication network 220. However, in other embodiments, the image database 205, the server 210, and the user device 215 communicate via one or more dedicated wire connection or other forms of wired and wireless electronic communication.

The image database 205 includes a memory 216 (a non-transitory, computer-readable medium) storing a plurality of medical images 217. In some embodiments, the image database 205 may be combined with the server 210, the user device 215 or a combination thereof. Also, in some embodiments, the medical images 217 may be stored within a plurality of databases, some of which may be included in the server 210. Although not illustrated in FIG. 2, the image database 205 may include a communication interface (similar to the communication interface included in the server 210 as described below) configured to communicate over the communication network 220.

The server 210 includes a plurality of electrical and electronic components that provide power, operational control, and protection of the components within the server 210. For example, as illustrated in FIG. 2, the server 210 includes an electronic processor 225, a memory 230, and a communication interface 235. The electronic processor 225, the memory 230, and the communication interface 235 are communicatively coupled via a wireless connection, a dedicated wired connection, a communication bus, or the like. Although FIG. 2 only illustrates one server 210, functionality performed by the server 210 as described herein may be distributed among multiple servers, including servers providing a cloud service. In some embodiments, the server 210 also performs functionality in addition to the functionality described herein. Further, the server 210 may further include additional components than those illustrated in FIG. 2, such as one or more human-machine interfaces.

The electronic processor 225 included in the server 210 may be a microprocessor, an application-specific integrated circuit (ASIC), or other suitable electronic device. The memory 230 includes non-transitory computer-readable medium, such as read-only memory ("ROM"), random access memory ("RAM") (e.g., dynamic RAM ("DRAM"), synchronous DRAM ("SDRAM"), and the like), electrically erasable programmable read-only memory ("EEPROM"), flash memory, a hard disk, a secure digital ("SD") card, other suitable memory devices, or a combination thereof. The electronic processor 225 accesses and executes computer-readable instructions ("software") stored in the memory 230. The software may include firmware, one or more applications, program data, filters, rules, one or more program modules, and other executable instructions. For example, the software may include instructions and associated data for performing a set of functions, including the methods described herein. In particular, as illustrated in FIG. 2, the memory 230 may store a reporting application 236. As described in more detail below, the reporting application 236 (when executed by the electronic processor 225) generates a user interface that allows a user to insert findings into a report template to generate an electronic report, such as a radiology report for a set of medical images.

The communication interface 235 allows the server 210 to communicate with devices external to the server 210. For example, as illustrated in FIG. 2, the server 210 may communicate with the image database 205, the user device 215, and other computing resources through the communication interface 235. The communication interface 235 may include a port for receiving a wired connection to an external device (e.g., a universal serial bus ("USB") cable and the like), a transceiver for establishing a wireless connection to an external device (e.g., over one or more communication networks 220, such as the Internet, a local area network ("LAN"), a wide area network ("WAN"), and the like), or a combination thereof.

The user device 215 may be a desktop computer, a laptop computer, a smartphone, a tablet computer, a smart television, a smart wearable, and the like. The user device 215 may include similar components as the server 210. For example, as illustrated in FIG. 2, the user device 215 includes an electronic processor 245, memory 250, and communication interface 255, which may be communicatively coupled via a wireless connection, a dedicated wired connection, a communication bus, or the like. Although FIG. 2 only illustrates one user device 215, the system 200 may include multiple user devices. In particular, multiple user devices 215 may communicate with the server 210 to access and use the reporting application 236. In some embodiments, the user device 215 performs functionality in addition to the functionality described herein. Further, the user device 215 may further include additional components than those illustrated in FIG. 2. The user device 215 also includes one or more human-machine interfaces (HMIs) 260. The human-machine interfaces 260 may include one or more input devices, such as a touch-screen, a mouse, a keyboard, a computer screen, a microphone, and the like.

A user may use the user device 215 to access medical images and generate an electronic report for the medical images. For example, the user may access medical images 217 from the image database 205 and may access the reporting application 236 executed by the server 210 (through a browser application or a dedicated application stored on the user device 215) to generate an electronic report for the medical images 217. As noted above, in some embodiments, the image database 205 may be included in the server 210, such that the user device 215 communicates with the server 210 to both access medical images and generate a report. Also, in some embodiments, the medical images 217, the reporting application 236, or both are locally stored and executed by the user device 215.

As noted above, when a user generates an electronic report, the user's attention is divided between images 217 and a report interface generated by the reporting application 236. To solve this and other problems, the system 200 is configured to automatically place user input into a section of the electronic report (a report template) so that the user can stay focused on the images 217.

Figure 3:
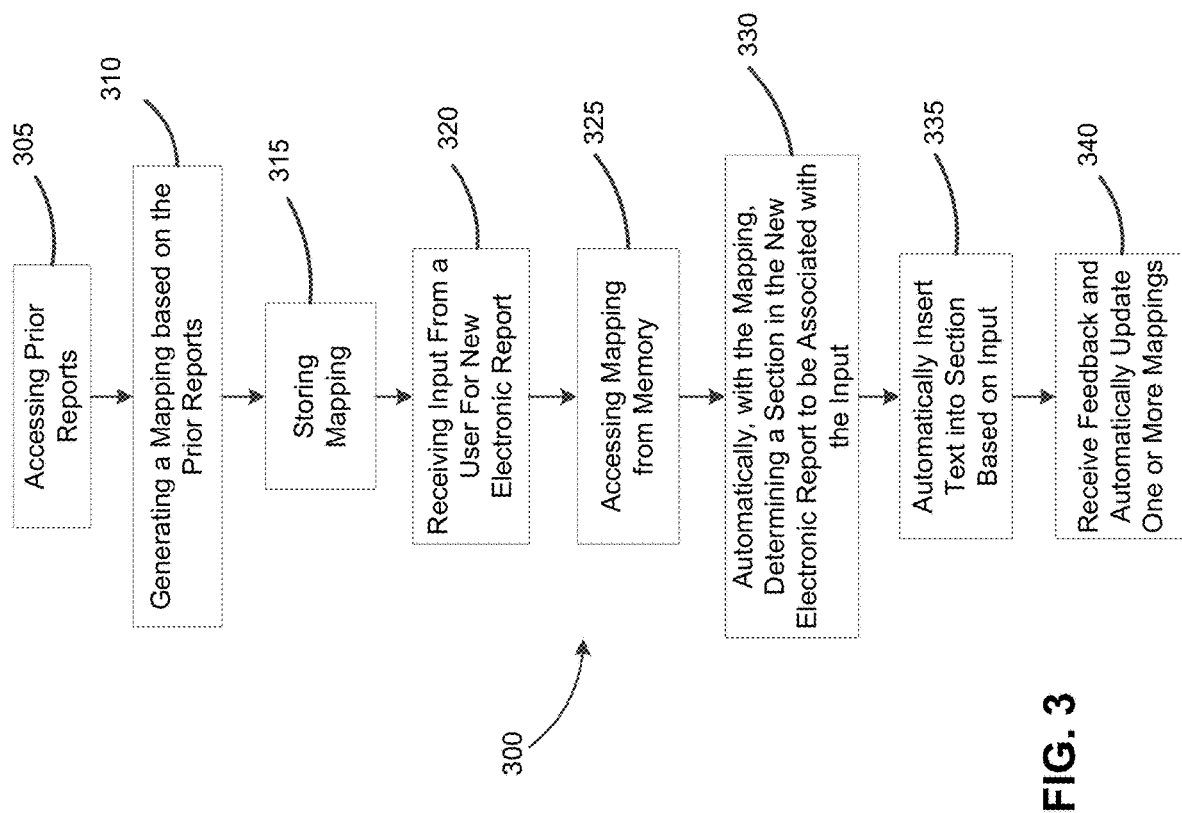
FIG. 3 is a flowchart of a method of generating an electronic report performed by the system of FIG. 2 according to one embodiment.

For example, FIG. 3 is a flowchart of a method 300 for generating an electronic report for a set of medical images. The method 300 is described as being performed by the server 210 (by the electronic processor 225 executing the reporting application 236). However, as noted above, in some embodiments, all or a portion of the functionality included in the method 300 may be performed by the user device 215, another server, or a combination thereof.

As illustrated in FIG. 3, the method 300 includes accessing a plurality of prior reports associated with a user (at block 305). The prior reports may be stored in the image database 205, the server 210 (the memory 230 or a separate memory), the user device 215, within a cloud computing environment accessible via the communication network 220, on a different server, or a combination thereof. The prior reports associated with the user may be reports the user has generated, has reviewed in the past, has approved in the past, or has in some way interacted with or been involved with in the past. In some embodiments, the prior reports associated with the user also includes reports generated, reviewed, or analyzed by other users, such as other users in the user's department, clinic, healthcare network, and the like. For example, in some situations, such as the user being new, a user may not have generated a large number of reports. Accordingly, in these situations, prior reports associated with similarly-situated users may be accessed and used to generate one or more mappings for the user as described herein. In some embodiments, a user manually selects the plurality of prior reports. In other embodiments, the reporting application 236 may be configured to automatically select the plurality of prior reports or a portion thereof, which may be presented to a user for approval or modification.

The method 300 further includes automatically generating at least one mapping based on the prior reports (at block 310). The mapping associates language (one or more terms, phrases, meanings, concepts, or a combination thereof) with at least one section of a structured report template. The electronic processor 225 generates the mappings using machine learning. Machine learning generally refers to the ability of a computer program to learn without being explicitly programmed. In some embodiments, a computer program (for example, a learning engine) is configured to construct a model (for example, one or more algorithms) based on example inputs. Supervised learning involves presenting a computer program with example inputs and their desired (for example, actual) outputs. The computer program is configured to learn a general rule (for example, a model) that maps the inputs to the outputs. The computer program may be configured to perform machine learning using various types of methods and mechanisms. For example, the computer program may perform machine learning using decision tree learning, association rule learning, artificial neural networks, inductive logic programming, support vector machines, clustering, Bayesian networks, reinforcement learning, representation learning, similarity and metric learning, sparse dictionary learning, and genetic algorithms. Using all of these approaches, a computer program may ingest, parse, and understand data and progressively refine models for data analytics.

For example, to generate a mapping, the server 210 may access prior reports for a particular type of imaging exam and use one or more machine learning techniques to develop a model that maps particular language (terms, phrases, meanings, concepts, and the like) to particular sections of an electronic report (a structured report template). In particular, in one embodiment, the server 210 parses a plurality of prior reports using machine learning to identify common language (one or more terms, phrases, meanings, concepts, or a combination thereof) associated with particular sections of an electronic report, such as fields of a report template. For example, using machine learning, the server 210 may automatically determine that the user repeatedly includes the phrase "the medial meniscus of the knee has a partial tear" in the section in a knee MRI report and, more particularly, in a medial meniscus section of such a report. Thus, in this example, a mapping generated by the server 210 includes an association (a customized hierarchy of language or metadata) between the phrase "the medial meniscus of the knee has a partial tear" and the meniscus section of a knee MM report.

In some embodiments, a mapping stores language and an identifier of one or more sections of an electronic report (template sections), such as in a look-up table, table, graph, or other data structure. The identifier of the one or more sections of an electronic report may include a field name, a template location, a template name, and the like. The stored language may include a string or a plurality of strings. For example, in some embodiments, the server 210 parses user input into a plurality of tokens. In particular, using the above example, the server 210 may parse the phrase "left ventricle of the heart has a large aneurysm" into "left ventricle," "of the," "heart," "has a," and "large aneurysm." Similarly, in some embodiments, the stored language may include only a portion of user input. In particular, the server 210 may not store articles ("a," "an," or "the") or other portions of language that are optional or may vary. These portions may similarly be represented as wildcards or optional text. Also, in some embodiments, the server 210 may store multiple versions of language within a mapping. For example, the server 210 may generate a mapping such that the phrases "Normal with no visible mass," "Normal—no visible mass," "Normal, no visible mass," and "Normal no mass" all map to the same section of a report template. As described in more detail below, storing tokenized input, wildcards, or alternative language may allow the server 210 to better map user input to a particular section of an electronic report even when the user input does not match language included in a mapping verbatim.

In some embodiments, a mapping may also associate language with a particular knowledge base. For example, a mapping may indicate that input including the term "cranial" should be interpreted using a particular knowledge base (dictionary, natural language processing module, or the like). Accordingly, a mapping may define multiple levels of association to aid the identification of a report section with particular user input.

The server 210 may generate a single mapping for a user or may generate a plurality of mappings for a user. For example, in one embodiment, the server 210 may determine a mapping for a user for different types of electronic reports generated by the user, different types of medical images, different anatomy, different roles of a user, different modalities capturing the medical images analyzed within a report, and the like. Also, in some embodiments, a mapping may be associated with multiple users. For example, the server 210 may generate a mapping as described above using prior reports of multiple users, such as users working at the same clinic, located in the same geographic location, or the like.

After the server generates a mapping for a user (at block 310), the server 210 stores the mapping (at block 315). The server 210 may store the mapping locally (in the memory 230), in the image database 205, on the user device 215, on a separate server, within a cloud computing environment, or a combination thereof. After the mapping is generated and stored (at blocks 310 and 315), the mapping is available for use to create new electronic reports for medical images. In particular, when a user provides input for a new electronic report (which may include modifying an existing electronic report), the server 210 accesses the stored mapping and applies the mapping to automatically populate an electronic report based on input from the user (at block 320 and 325, respectively). In some embodiments, the server 210 automatically accesses the stored mapping by identifying the user generating the report and accessing the appropriate stored mapping. In other embodiments, the server 210 prompts the user whether a stored mapping should be used and may allow the user to select the stored mapping, such as from a list of available mappings. Also, the server 210 may access the stored mapping before or after a user provides input for a new electronic report.

In some embodiments, the server 210 applies one or more selection rules to select a mapping for a user. For example, the server 210 may be configured select a mapping based on a role of the user, the type of report being generated, the type of images being reviewed, the exam type, patient attributes, the imaging modality used, the location of service, and the like. For example, when the server 210 determines that the image is a heart image, the server 210 may select and access a mapping that is specific for heart images. In particular, in some embodiments, each available report template may have an associated mapping. Therefore, the server 210 may be configured to determine the applicable report template to determine applicable mapping. In some embodiments, a user may manually select a report template. In other embodiments, the server 210 may be configured to automatically select a report template based on the images, the user, or other contextual information. The selection rules may be defined as part of generating a mapping. For example, when generating a mapping, prior reports may be fed to the server 210 that satisfy particular parameters (user, user role, exam type, and the like). Accordingly, these parameters may define the selection rules or selection parameters for the resulting mapping generated by the server 210.

After selecting an appropriate mapping, the server 210 processes input from the user using the mapping to automatically determine a section in the new electronic report to be associated with the input (at block 330). The user input may be received through the HMI 260. For example, the user input may be audio data captured by a microphone (dictated report findings), text data received from a keyboard, a selected option received through a user interface of the user device 215 (via a mouse, a touchscreen, or the like), or a combination thereof. In some embodiments, when the input includes audio data, the server 210 is configured to convert the audio data into text data using natural language processing. The server 210 may also perform additional processing of the user input, such as tokenizing the user input as described above for generating the mappings.

To process the input, the server 210 determines a match between the input (or a portion thereof) and language included in the accessed mapping. As noted above, language in a mapping may include one or more terms, phrases, meanings, concepts, or a combination thereof. For example, when the input includes the phrase "1.5×1.7 centimeter enhancing temporal lobe mass," the server 210 compares this phrase to language included in the mapping. In particular, the mapping may associate the phrase "in the temporal lobe" with the "Cerebrum" section of an electronic report. In some embodiments, the server 210 may determine the best match between the user input and language included in the mapping. For example, the server 210 may tokenize user input and determine terms included in the mapping matching the highest number or percentage of tokens. In other embodiments, the server 210 may identify language included in the mapping matching user input in terms of number of words, order of words, presence of key words, meaning, concepts, and the like.

After identifying a section of the electronic report for the user input, the server 210 automatically inserts text into the identified section of the new electronic report (at block 335). For example, continuing with the same example from above, the server 210 may add the text "1.5×1.7 centimeter enhancing temporal lobe mass" to the "Cerebrum" section of the electronic report. In some embodiments, the server 210 inserts the user input (or a portion thereof) into the electronic report as received from the user. In other embodiments, the server 210 modifies the user input before insertion. For example, in some embodiments, the server 210 removes words or phrases from the user input that are redundant. In particular, when the user input includes the phrase "tumor along the dorsal margin of the spinal cord" and the determined section of the report for this phrase is titled "Spinal Cord," the server 210 may delete the words "of the spinal cord" from the text interested into the report. Similarly, in some embodiments, the server 210 inserts the language from the mapping in place of the input received from the user. It should be understood that, in some embodiments, the server 210 is configured to add a section to an electronic report associated with user input in situations where the electronic report does not already include the section. Thus, as described in more detail below, the server 210 may be configured to dynamically build or customize an electronic report based on user input. FIG. 4 illustrates a sample electronic report 350 generated by the server 210 using the method 300.

When applying mappings, the server 210 may be configured to apply one or more insertion rules. The insertion rules may adjudicate conflicts, such as instances where the user inputs a phrase that includes language that a mapping associates with two different sections of an electronic report. The insertion rules may determine what sections should govern or whether the phrase should be inserted in both sections. The insertion rules may consider contextual information. For example, the insertion rules may consider the text inserted in various sections of the electronic report, such as whether one of the identified sections already includes text. Similarly, the insertion rules may dictate whether existing text included in a section should be overridden by subsequent user input based on a mapping or whether the subsequent input should be moved to another section or appended to the existing text.

Similarly, in some embodiments, the insertion rules also modify a structured report template based on received user input. For example, the insertion may define a preferred order of report fields, which may dynamically vary based on user input. In particular, the insertion rules may be configured to move predetermined findings (such as abnormal findings) to the beginning of a report, the end of the report, or a predetermined position within a report. For example, in some embodiments, a user can start with a blank report template, which may be built as the user provides input. Alternatively or in addition, sections of a report template may be deleted based on user input. Similarly, in some embodiments, the insertion rules may emphasis or otherwise flag particular findings (or other user input) as "important" or needing additional attention or may automatically add particular user input to a summary or conclusion section of a report.

Also, in some embodiments, the insertion rules further define one or more automatic actions to take in response to user input. For example, when user input requires further attention, the server 210 may automatically generate one or more warnings or alerts, including sending an email message to an ordering physician or the like, automatically scheduling a follow-up procedure or consultation, or the like.

It should be understood that, in some embodiments, the server 210 generates insertion rules as part of generating a mapping. Alternatively or in addition, the server 210 may generate insertion rules based on user feedback as described below or through manual configuration. Accordingly, the mappings, selection rules, and insertion rules, or a combination thereof establish customized report templates for individual users or groups of users, create report preferences for individual users or groups of users, and the like. Thus, using the mappings, selections rules, and insertion rules, a user may be able to freely provide input (dictate) findings (using preferred language, a preferred order, a preferred format, a preferred template, and the like) to create a completed electronic report.

In some embodiments, the server 210 allows a user to validate or confirm text automatically inserted into the new electronic report. For example, as the server 210 populates the electronic report or when the user is finished reviewing the medical image, the user may access the populated electronic review and manually update the electronic report as desired. Optionally, the server 210 receives this feedback and automatically updates (using machine learning) one or more stored mappings (at block 340). For example, when the server 210 populated the "Cerebrum" section of a report with the text "1.5×1.7 centimeter enhancing temporal lobe mass" but the user manually moves (or duplicates) this text to a different section of the electronic report, the server 210 tracks these manual changes and automatically applies them to the stored mapping (through the mapping itself or an associated insertion rule). In particular, the server 210 may associate the inserted text with another or a different report section. In this way, the mappings automatically learn and adapt to user preferences and requirements even as these preferences change over time.

Figure 5:
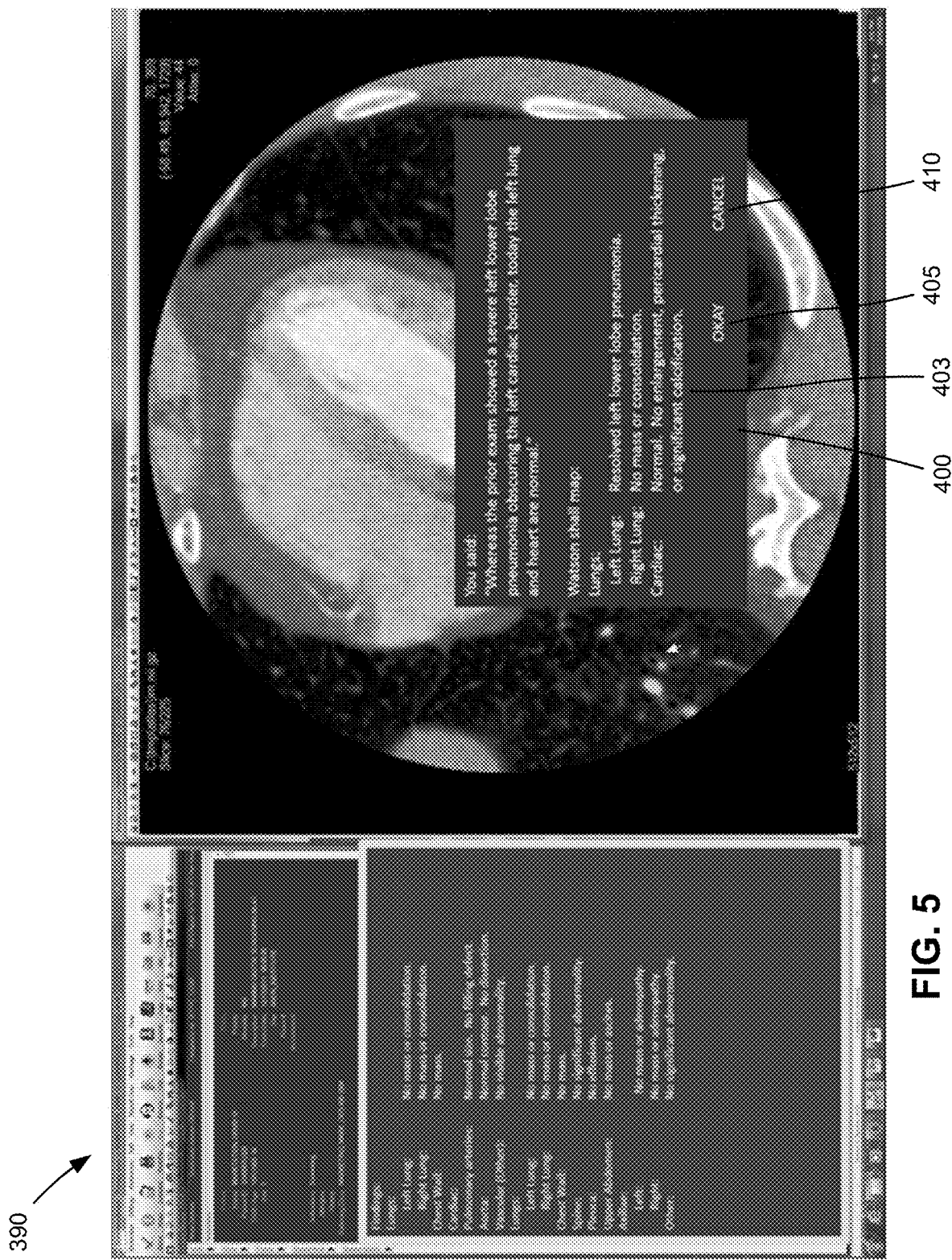
FIG. 5 illustrates a user interface including a validation window generated by the system of FIG. 2 according to one embodiment.

In some embodiments, the server 210 is also configured to preview automatically inserted text for a user and allow a user to validate or confirm the automatically inserted text. For example, FIG. 5 illustrates a user interface 390 generated by the server 210 that includes a validation window 400. The validation window 400 includes a dialog box 403 that includes text to be inserted in the section of the electronic report as determined by the server 210. The dialog box 403 may also specify the section of the report where the text will be inserted. In some embodiments, the dialog box 403 also includes the original user input. The validation window 400 also includes one or more selection mechanisms (buttons, checkboxes, radio buttons, and the like) for validating or confirming the text to be inserted, the section of the report, or both. For example, as illustrated in FIG. 5, the validation window 400 may include a confirm selection mechanism 405 and a reject selection mechanism 410. In response to the user selecting the confirm selection mechanism 405, the server 210 automatically inserts the designated text into the designated section of the report as described above. In response to the user selecting the reject selection mechanism 410, the server 210 does not insert the designated text into the designated section. In this situation, the server 210 may also be configured to prompt the user (textually, audibly, or a combination thereof) for one or more changes to the designated text, the designated section, or both, and the server 210 may automatically populate the report based on the received changes.

As illustrated in FIG. 5, the server 210 may output the validation window 400 as a pop-up window displayed on top of a displayed medical image. In other embodiments, the validation window 400 may be displayed in other user interfaces or areas of a user interface. However, displaying the validation window 400 within a displayed image may keep the user's attention on the image. The functionality provided via the validation window 400 may also be achieved in other ways. For example, in some embodiments, the designated text and section may be audibly output and the user may be audibly prompted to confirm or reject the designated text, section, or both (via voice commands). Furthermore, the server 210 may provide the validation window at different times during generation of an electronic report. For example, the server 210 may be configured to provide validation windows 400 when a section is determined for user input, when a user switches to a new image, when a user indicates that a report is complete, or the like.

The server 210 may similarly use the validation window 400 to resolve conflicts. For example, the server 210 may receive input of "Whereas the prior exam showed a severe left lower lobe pneumonia obscuring the left cardiac border, today the left lung and heart are normal," as illustrated in FIG. 5, and may determine that the language included in this input is associated with both a lung section and a cardiac section of a report template. Thus, the server 210 may not be able to correctly identify where to place the received input. Accordingly, to resolve such conflicts, the server 210 may provide a validation window 400 as described above that indicates possible placements for received input and prompts a user to select one of the destinations (or reject all the destinations). Similarly, in a situation where the server 210 cannot identify any possible destinations for user input based on a mapping, the server 210 may generate a list of potential destinations, which may include a list of report sections not yet complete, a list of all report sections, the last sections of the report where text was inserted, a list of sections where similar language has been placed in past reports, and the like. The server 210 may also be configured to update the mappings, insertion rules, or both as described above based on feedback received through the validation window 400.

Thus, embodiments described herein provide methods and systems for automatically associating user input with sections of an electronic report for a medical image using machine learning. By accessing prior reports, the systems and methods using machine learning to automatically create mappings that define a section of a report template for particular user input. Thus, a user does not have to shift focus between medical images and the new report. Similarly, by using machine learning, the systems and methods do not require laborious configuration that must be repeated for each user to provide a customized experience. Furthermore, by tracking manual modifications to text automatically inserted into a report template, the systems and methods automatically learn and adapt to a user's changing practice. Although embodiments are described herein with respect to electronic reports for medical images, the methods and systems described herein may be used with electronic reports and documents associated with other subject matter both within and outside of the field of healthcare.

Various features and advantages are set forth in the following claims.

What is claimed is:

1. A system for generating electronic reports for medical images, the system comprising:
   an electronic processor configured to
      access a plurality of prior reports associated with a user,
      automatically generate a mapping using machine learning based on the plurality of prior reports, the mapping associating language included in the plurality of prior reports with at least one section of a report,
      store the mapping to a memory,
      receive input from the user for an electronic report associated with a medical image, wherein the input is a dictated report finding,
      tokenize the input by parsing the input into a plurality of tokens,
      access the mapping from the memory,
      automatically determine a section in the electronic report to be associated with the input without receiving a selection of the section from the user based on the mapping by determining if the tokenized input satisfies a matching condition associated with the mapping,
      automatically insert text into the section in the electronic report based on the input,
      receive feedback associated with the text inserted into the section in the electronic report, and
      automatically update the mapping based on the feedback.

2. The system of claim 1, wherein the plurality of prior reports associated with the user includes at least one prior report generated by the user.

3. The system of claim 1, wherein the plurality of prior reports associated with the user includes at least one prior report generated by a second user.

4. The system of claim 1, wherein the electronic processor is configured to access the plurality of prior reports based on a manual selection of the plurality of prior reports received from the user.

5. The system of claim 1, wherein the electronic processor is configured to access the mapping from the memory by applying a selection rule.

6. The system of claim 5, wherein the selection rule specifies at least one selected from a group consisting of a role of the user, a type of the electronic report, and a type of the medical image.

7. The system of claim 1, wherein the electronic processor is configured to automatically insert the text into the section in the electronic report based on the input by inserting at least one term included in the mapping into the section.

8. The system of claim 1, wherein the electronic processor is configured to automatically insert the text into the section in the electronic report based on the input by inserting the input into the section.

9. The system of claim 1, wherein the electronic processor is further configured to, before inserting the text into the section of the electronic report, automatically generate and display a window, the window including the text to be inserted into the section of the electronic report, an identifier of the section of the electronic report, and a selection mechanism for validating the text to be inserted into the section of the electronic report, and wherein the electronic processor is configured to automatically insert the text into the section in the electronic report based on the input in response to selection of the selection mechanism.

10. The system of claim 9, wherein the window is displayed within the medical image.

11. The system of claim 9, wherein the window includes a second selection mechanism for rejecting the text to be inserted into the section of the electronic report.

12. The system of claim 9, wherein the window includes an input mechanism for modifying the section of the electronic report.

13. The system of claim 1, wherein the mapping is associated with a plurality of users including the user.

14. The system of claim 1, wherein the electronic processor is further configured to dynamically add the section of the electronic report based on the input.

15. A method of generating electronic reports for medical images, the method comprising:
   accessing, with an electronic processor, a plurality of prior reports associated with a user;
   automatically, with the electronic processor, generating a mapping using machine learning based on the plurality of prior reports, the mapping associating language included in the plurality of prior reports with at least one section of a report;
   storing the mapping to a memory;
   receiving input from the user for an electronic report associated with a medical image, wherein the input is a dictated report finding;
   accessing the mapping from the memory;
   automatically determining a section in the electronic report associated with the input based on the mapping without receiving a selection of the section from the user;
   automatically generating and displaying a window, the window including text to be inserted into the section of the electronic report, an identifier of the section of the electronic report, and a selection mechanism for validating the text to be inserted into the section of the electronic report, wherein the text is the input as received; and
   automatically inserting the text into the section in the electronic report based on the input in response to selection of the selection mechanism.

16. The method of claim 15, wherein automatically generating and displaying the window includes automatically generating and displaying the window within the medical image.

17. The method of claim 15, further comprising receiving feedback through the window and automatically updating the mapping based on the feedback.

18. A non-transitory, computer-readable medium storing instructions that, when executed by an electronic processor, perform a set of functions, the set of functions comprising:
   accessing a plurality of prior reports associated with a user;
   automatically generating a plurality of mappings using machine learning based on the plurality of prior reports, each mapping of the plurality of mappings associating language included in the plurality of prior reports with at least one section of a report;
   storing the plurality of mappings to a memory;
   receiving input from the user for an electronic report associated with a medical image, wherein the input is a dictated report finding;
   accessing the plurality of mappings from the memory;
   in response to determining the input applies to two or more mappings of the plurality of mappings, wherein each mapping is associated with a different section of the electronic report, automatically selecting one mapping of the two or more mappings based on an insertion rule associated with the user and determining a section in the electronic report associated with the input based on the selected one mapping without receiving a prior selection of the section from the user;
   prompting the user to validate the determined section;
   in response to validating the determined section, automatically inserting text into the determined section in the electronic report based on the input;
   receiving feedback associated with the text; and
   automatically updating the mapping based on feedback.

19. The system of claim 1, wherein the matching condition is a matching condition selected from a group consisting of a highest number of matches, a highest percentage of matches, a number of words, an order of words, a presence of one or more key words, a meaning, and a concept.

* * * * *